US012611491B2

(12) United States Patent
Flanagan et al.

(10) Patent No.: US 12,611,491 B2
(45) Date of Patent: *Apr. 28, 2026

(54) USE OF NANOCRYSTALS FOR DRUG DELIVERY FROM A BALLOON

(71) Applicant: BOSTON SCIENTIFIC SCIMED, INC., Maple Grove, MN (US)

(72) Inventors: Aiden Flanagan, County Galway (IE); Jan Weber, Maastricht (NL); John Clarke, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/699,265

(22) Filed: Mar. 21, 2022

(65) Prior Publication Data

US 2022/0211918 A1      Jul. 7, 2022

Related U.S. Application Data

(63) Continuation of application No. 16/533,263, filed on Aug. 6, 2019, now Pat. No. 11,278,648, which is a continuation of application No. 12/815,158, filed on Jun. 14, 2010, now Pat. No. 10,369,256.

(60) Provisional application No. 61/224,723, filed on Jul. 10, 2009.

(51) Int. Cl.
A61L 29/16          (2006.01)

(52) U.S. Cl.
CPC ......... *A61L 29/16* (2013.01); *A61L 2300/416* (2013.01); *A61L 2300/624* (2013.01); *A61L 2300/63* (2013.01)

(58) Field of Classification Search
CPC ........ A61L 29/16; A61L 31/196; A61L 31/29; A61L 31/26
See application file for complete search history.

(56) References Cited

U.S. PATENT DOCUMENTS

| | | | | |
|---|---|---|---|---|
| 11,278,648 | B2 * | 3/2022 | Flanagan ................ | A61L 29/16 |
| 2006/0088596 | A1 * | 4/2006 | Labrecque ............ | A61K 47/44 |
| | | | | 424/472 |
| 2007/0154554 | A1 * | 7/2007 | Burgermeister ....... | A61K 31/65 |
| | | | | 424/486 |
| 2008/0071352 | A1 * | 3/2008 | Weber ..................... | A61L 31/16 |
| | | | | 623/1.42 |
| 2008/0118544 | A1 * | 5/2008 | Wang ..................... | A61P 11/00 |
| | | | | 424/448 |
| 2009/0029077 | A1 * | 1/2009 | Atanasoska ........... | A61L 31/148 |
| | | | | 428/34.1 |

FOREIGN PATENT DOCUMENTS

| | | | | | | |
|---|---|---|---|---|---|---|
| CA | | 2659089 | A1 * | 1/2008 | ............ | A61M 39/10 |
| CA | | 2672496 | A1 * | 6/2008 | ............... | A61F 2/16 |
| CA | | 2695089 | A1 * | 2/2009 | ............ | A61L 29/08 |
| WO | WO-2008070996 | A1 * | 6/2008 | ............ | A61L 31/10 |
| WO | WO-2008131131 | A1 * | 10/2008 | ............... | A61F 2/82 |

* cited by examiner

*Primary Examiner* — Micah Paul Young
(74) *Attorney, Agent, or Firm* — Seager, Tufte & Wickhem, LLP

(57)          ABSTRACT

A drug delivery balloon (10) has a drug thereon in the form of crystalline particles (12), the drug having a predetermined size distribution. Optionally marker particles (14, 16) are also provided. A texturized coating (18), a cap layer (20) and/or other methods may be used to increase particle loading capacity of the balloon.

14 Claims, 2 Drawing Sheets

USE OF NANOCRYSTALS FOR DRUG DELIVERY FROM A BALLOON

CROSS-REFERENCE TO RELATED APPLICATIONS

This application is a continuation of U.S. application Ser. No. 16/533,263, filed Aug. 6, 2019, which is a continuation of U.S. application Ser. No. 12/815,158, filed Jun. 14, 2010; which claims the benefit of priority under 35 U.S.C. § 119 to U.S. Provisional Application Ser. No. 61/224,723 filed on Jul. 10, 2009, the entire contents of which are hereby incorporated by reference.

BACKGROUND OF THE INVENTION

Balloons coated with paclitaxel containing formulations are known. In some cases paclitaxel has been applied directly to the balloon or to a coating placed on the balloon. In other cases paclitaxel has been formulated with an excipient that may be polymer, a contrast agent, a surface active agent, or other small molecules that facilitate adhesion to the balloon and/or release from the balloon upon expansion. The formulations have typically been applied from solution, and may be applied to the entire balloon or to a folded balloon, either by spraying, immersion or by pipette along the fold lines.

Paclitaxel coated balloons that provide high release rates from the balloon surface have recently been developed. However these balloons do not yet provide for delivery of predictable amounts of the drug to the tissue at the delivery site nor do they provide for a predictable therapeutic drug tissue level over an extended time period.

In regards to drug delivery from a balloon, currently a mixture of a drug (paclitaxel) and a secondary substance in solution is sprayed or dip-coated on a balloon surface and dried, creating a solid matrix of the two components on the balloon surface which breaks off in undefined and sometimes very large pieces upon deployment of the balloon. These pieces can be up to hundreds of micrometers. A variety of negative effects can as such be described.

a/ The distribution of the particles over the vessel wall is non-uniform. Having large chucks at one place automatically means a void at other places.

b/ The uptake into the tissue is different as it is known that single micrometer sized and nano-sized particles are better absorbed by cells. So, with the current matrix breaking up in a wide distribution of chunks part will be absorbed and part will hang on the wall or float downstream.

Furthermore having the drug being sprayed in solution causes the drug to be present in the final coating on the balloon surface in an unknown mixture of amorphous and crystalline nature. It is known, however, that a crystalline or amorphous morphology of paclitaxel greatly affects the extended release kinetics of the drug in tissue.

SUMMARY OF THE INVENTION

The invention addresses problems both with the morphological form of the drug and the reproducibility of the particles delivered by a drug delivery balloon. The invention uses nano-crystalline particles of a drug component to provide for a controlled morphology and particle size. According to the invention, the drug is put into a preferred size and morphology before it is applied to the balloon, and the particles are loaded onto the balloon in a manner that preserves these features during application process.

One aspect of the invention pertains to a drug delivery balloon adapted for delivery of a drug to a site in a body passageway, the balloon comprising a balloon wall with an outer surface, and the balloon having a drug disposed on the outer surface, wherein the drug is provided on the balloon as crystalline particles of said drug in a predetermined size distribution.

In some embodiments the drug is provided as a mixture at least two different narrow size distributions, selected to provide a tissue residence of the drug at the application site In some aspects the nanocrystalline drug particles are accompanied in a predetermined ratio with marker particles that allow for the monitoring of the delivery location and dosage.

Other aspects of the invention pertain to methods of increasing particle capacity of the balloons.

In another aspect the invention pertains to a drug delivery balloon comprising a coating thereon and a drug applied over the coating, wherein the coating has a textured surface that increases the drug carrying capacity of the balloon.

Still other aspects of the invention are described in the Figures, the Detailed Description of Preferred Embodiments and/or in the Claims below.

DETAILED DESCRIPTION OF PREFERRED EMBODIMENTS

Figure 1:
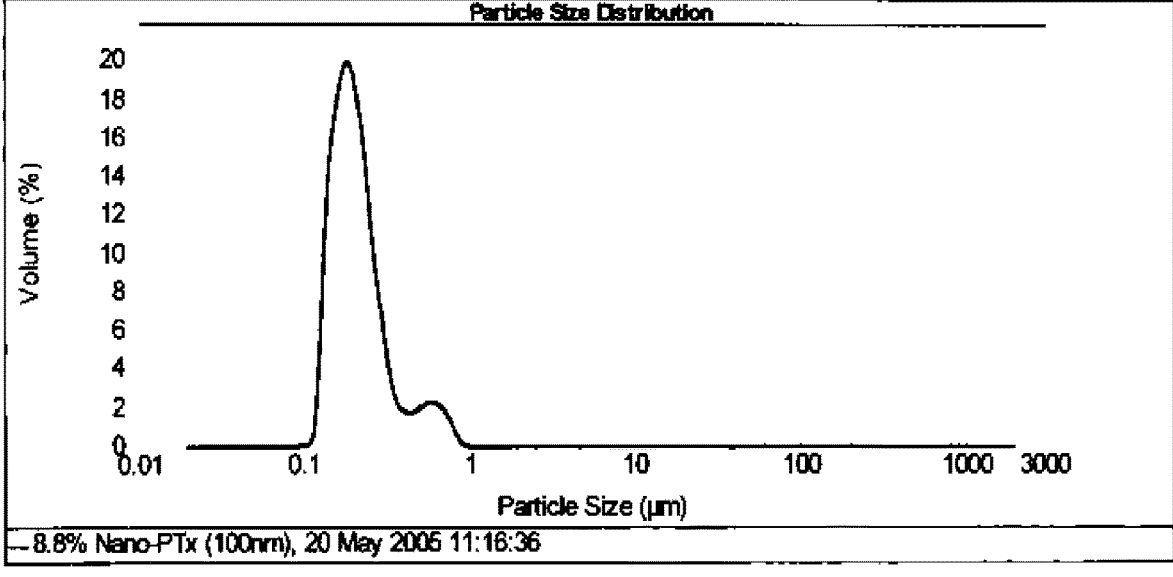
FIG. 1 Graph showing particle size distribution of exemplary paclitaxel crystalline particles.

As used herein the term drug delivery balloon pertains to a balloon that has an outer surface coating that carries a drug that is delivered to a tissue site when a device carrying the balloon is provided at the tissue site and the balloon is expanded. The drug coating may be part of a single or multilayered system and the drug may be accompanied by various excipient substances that facilitate retention during delivery and/or release of the drug from the balloon surface.

According to the invention a drug delivery balloon is provided as particles of said drug of a controlled size distribution. In at least some embodiments the drug particles comprise greater than 90%, for instance at least 95%, at least 98% or at least 99% of the drug.

Drug particles useful in the invention may be prepared from crystalline drug form material obtained in any suitable manner which is ground or milled to the desired size. In some instances cryogrinding, e.g. at temperatures of –40° C. or less, may be useful. Sieving or other classification techniques can be used to confine the distribution of the particles to a desired range. This allows the size distribution of the crystalline particles to be controlled precisely. In some embodiments the particles are substantially all about 1 µm or less. The particle size may be in the range of 0.01-2.0 µm (10-2000 nm). In at least some embodiments a narrower size range for instance 0.01-0.1 µm; 0.01-0.2 µm; 0.01-0.5 µm; 0.1-0.3 µm; 0.1-0.4 µm; 0.2-0.4 µm; 0.1-0.5 µm; 0.2-0.4 µm; 0.2-0.5 µm; 0.2-0.6 µm; 0.3-0.5 µm; 0.3-0.6 µm; 0.3-0.7 µm; 0.4-0.6 µm; 0.4-0.7 µm; 0.4-0.8 µm; 0.5-0.7 µm; 0.5-0.8 µm; 0.5-0.9 µm; 0.5-1.0 µm; 0.6-0.8 µm; 0.6-0.9 µm; 0.6-1.0 µm; 0.7-0.9 µm; 0.7-1.0 µm, 0.7-1.1 µm; 0.8-1.0 µm; 0.8-1.1 µm; 0.8-1.2 µm; 0.9-1.1 µm; 0.9-1.3 µm; 1.0-1.3 µm; 1.0-1.5 µm; 1.0-2.0 µm; 1.5-2.0 µm, is employed. By providing the drug in a specific particle size range the dosage at the tissue site will be more predictable than is currently provided from drug delivery balloons.

Multi-modal ranges, prepared, e.g by mixing two or more sets of different narrow size range may be used in some cases to provide a desired bioavailability profile over time. For example 50% of the crystals can be of 1000 nm mean size and the other 50% could be 300 nm mean size. This embodiment enables a tailoring of the drug persistence in the vessel wall. The smaller crystals will more readily dissolve and enter the tissue for immediate effect and larger crystals will dissolve at a much slower rate enabling longer drug persistence.

In at least some embodiments the drug particles are not microcapsules (i.e. the drug particle does not include an encapsulant enclosing the drug). However, it is contemplated that the drug particles may be carried in an excipient layer and that the drug particles may comprise minor amount of additives that stabilize the particles against agglomeration by surface adsorption of selected stabilizers. Suitable stabilizers may be a GRAS (Generally Regarded As Safe) stabilizer, e.g. a GRAS surfactant, anti-block agent or the like. Such GRAS stabilizers are desirably employed in concentrations of less than 1% by weight of the drug particle and are typically applied after the particles have been milled to size.

The prepared particles remain intact as they are applied to the balloon. That is, they are not dissolved or melted during application. However, the particles may be dispersed in a liquid, e.g. aqueous, medium that also includes a excipient material. The excipient may be polymer, a contrast agent, a surface active agent, or other small molecule. The drug suitably will be is substantially insoluble in the excipient. In some embodiments the drug particle is formulated with an excipient. An excipient is an additive to a drug-containing layer that facilitates adhesion to the balloon and/or release from the balloon upon expansion. Suitably the excipient is a material that is very readily soluble in body fluids and in which the drug is not soluble.

In some embodiments the excipient may remain on the delivery device at the time of drug transfer but allow efficient transfer of the drug from the mixture. In some embodiments the excipient provides weak phase boundaries with the drug particles that are easily overcome when a balloon is expanded, regardless of whether the excipient remains on the device or initially leaves the device with the drug. In some embodiments the excipient substantially degrades or dissolves in the course of the deployment or during transfer of the drug from the device at the site of administration such that little or none of the excipient is detectable on the tissue after a short interval, for instance an interval of 2 days, 1 day, 12 hours, 4 hours, 1 hour, 30 minutes, 10 minutes or 1 minute. In some embodiments dissolution or degradation of the excipient during deployment provides porosities in the drug-containing layer by the time the device is at the site of administration.

Examples of excipient materials that may be used include sugars (e.g., mannitol), polysaccharides (e.g. heparin), citrate esters (e.g. tributyl citrate, triethyl citrate, acetyltributyl citrate and/or acetyltriethyl citrate), contrast agents (e.g. iopamide), water soluble polymers (e.g. polyvinyl pyrrolidone), pharmaceutically acceptable salts, and the like.

In some embodiments the drug containing layer is applied over an underlayer of material that has a high solubility in bodily fluids to undercut the drug facilitate breakup of the drug-containing layer upon balloon expansion. An example of a suitable underlayer material is pectin.

Numerous other excipients and additive compounds, protective polymer layers, underlayer materials and drugs are described in one or more of the following documents:

U.S. Pat. No. 5,102,402, Dror et al (Medtronic, Inc.)
U.S. Pat. No. 5,370,614, Amundson et al, (Medtronic, Inc.)
U.S. Pat. No. 5,954,706, Sahatjian (Boston Scientific Corp)
WO 00/32267, SciMed Life Systems; St Elizabeth's Medical Center (Palasis et al)
WO 00/45744, SciMed Life Systems (Yang et al)
R. Charles, et al, "Ceramide-Coated Balloon Catheters Limit Neointimal Hyperplasia After Stretch Injury in Cartoid Arteries," *Circ. Res.* 2000; 87; 282-288
U.S. Pat. No. 6,306,166, Barry et al, (SciMed Life Systems, Inc.)
US 2004/0073284, Bates et al (Cook, Inc; MED Inst, Inc.)
US 2006/0020243, Speck
WO 2008/003298 Hemoteq AG, (Hoffman et al)
WO 2008/086794 Hemoteq AG, (Hoffman et al)
US 2008/0118544, Wang
US 20080255509, Wang (Lutonix)
US 20080255510, Wang (Lutonix)

All incorporated herein by reference in their entirety. In some cases paclitaxel has been applied directly to the balloon or to a coating placed on the balloon. In other cases paclitaxel has been formulated with an excipient that may be polymer, a contrast agent, a surface active agent, or other small molecules that facilitate adhesion to the balloon and/or release from the balloon upon expansion. The formulations have typically been applied from solution, and may be applied to the entire balloon or to a folded balloon, either by spraying, immersion or by pipette along the fold lines.

The drug is one that has therapeutic benefit at a site reachable by a balloon carrying medical device such as a catheter, endoscope or the like, and that is desirably provided in a therapeutic dosage that lasts for at least several hours or days. Desirably the drug has a characterizable crystalline form that provides limited solubility in aqueous body fluids. In such case the particle will have a lifetime at the site that is at least partly a function of its size, for instance a lifetime of a therapeutically effective dosage of 5 days, 10 days, 20 days, 30 days or 40 days after delivery.

According to the invention the drug is one that has a characteristic crystalline forms. In some embodiments the drug is a crystallizable, lipophilic, substantially water insoluble drug. The drugs which can be used in embodiments of the present invention, can be any therapeutic agent or substance that has therapeutic benefit for local administration by delivery from a medical device inserted into the body. Specific examples of drugs include anti-restenosis and anti-angeogenic drugs delivered in conjunction with a dilatation of a constriction or lesion in the vascular system and/or with stent placement. Specific examples of such drugs include paclitaxel, rapamycin, everolimus and mixtures thereof. In the case of mixtures the particles of the various drugs may have the same or different size distributions. For instance if a first drug has a desired therapeutic benefit shortly upon contact, and a second drug requires a desired effect over longer period the particles of the first drug may be provided a smaller size relative to those of the second drug.

In some embodiments of the invention the drug is paclitaxel. Nanocrystalline particles of paclitaxel dihydrate can be obtained for example from Elan Drug Technologies, Monksland, Athlone, County Westmeath, Ireland (website: http://www.elandrugtechnologies.com/nav/14/). Referring to FIG. 1, there is shown a particle size distribution profile of a specific embodiment of nanocrystaline paclitaxel dehydrate useful in an embodiment of the invention.

The drug particles are provided on the surface of the balloon. As already mentioned other components may be provided in the drug particle layer, e.g. excipient materials that bind the particles to the balloon or to each other, or various materials that provide the balloon surface with higher effective surface area so as to increase the particle retention capacity of the balloon.

The use of particles of a narrow size distribution on drug delivery balloons also allows solution of another issue that arises with drug delivery from a balloon, namely to how to allow the physician to control the amount and area of the delivered drug amount. A small amount of traceable nanoparticles, desireably of essentially the same size profile so that the distribution on the balloon and in the body is propostional, may be mixed in the suspension of the nanocrystaline drug particles. The mixed drug particle/tracer particle suspension is then sprayed onto the balloon surface and dried. Traceable particles are for example those that can be detected by MM or X-Ray by ultrasound. With the release of the drug particles from the surface, one will have a simultaneous release of the tracer particles allowing detection of the density and placement of the drug release to the vessel wall. In case the physician determines that the coverage obtained was too low, the physician can redeploy the existing or a new balloon. This same tracer system also allows deploying a second balloon to an area close or directly adjacent to an already treated area and while avoiding overlap which if the drug has a risk of providing too high of a dose when applied in overlapping areas.

Reference is made to FIGS. 2-5 depicting various aspects of the invention. In FIG. 1 there is shown a portion 10 of a balloon surface that is covered with nanocrystalline drug particles 12 and tracer particles 14. The tracer particles may be particles detectable by any remote imaging means, for instance the particles 14 may detectable by MRI (e.g., magnetite), X-Ray (e.g. Gold) or by ultrasound (e.g. air containing urethane capsules). The tracer particles and are preferably present in a known ratio relative to the drug particles 12 so that both the location and concentration of the drug particles can be estimated.

Figure 2:
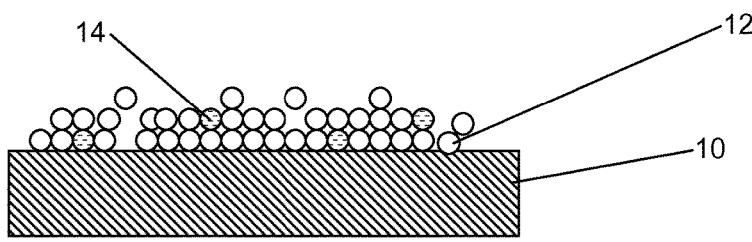
FIG. 2 Schematic depiction of a balloon surface coated with nanocrystalline drug particles and tracer particles.

FIG. 2 is similar to FIG. 1 except that a second different type of tracer particles 16 are also provided allowing detection by multiple techniques. This allows more flexibility to the physician in detection and in optimization of quantification. Of, course it is also possible to include even more than two different types of detectable particles without departing from the invention.

In some embodiments the drug particles are suspended in an aqueous media, that may optionally also contain dissolved matrix materials, and the particle suspension sprayed or dip-coated directly onto the balloon surface and dried. In this way the form of the crystals is not affected. Because the particles remain intact the residence time after delivery will be more predictable and dependent on an analysis of the particles that can be done before the balloon is prepared.

Another method of application of the drug particles is to use electrostatic attraction. For instance, a balloon made of a suitable polymeric material (such as a nylon, PET or Pebax® resin) is provided with an electrostatic charge in a manner similar to a van de Graaf generator. The nanocrystalline drug particle powder, is sprayed on a Teflon surface as an aqueous suspension and then dried. The charged balloon is swept just above the powdered surface to attract a coating of the dried powder.

The amount of drug that would be needed is such that a multi-layer of nanoparticles should be deposited on the balloon. Current 1st generation designs of paclitaxel delivery balloons have a payload of 3 microgram/mm$^2$ of which by the way up to 80% is lost during tracking the catheter through the artery. In some embodiments a drug coating of paclitaxel on a balloon contains from 100 to 1000 µg of paclitaxel, for instance 200-800 µg, 300-600 µg, or 400-500 µg of paclitaxel. These dosages may require a coating depth on the balloon of as much as 3 micrometers, or more.

There are various ways to increase the payload a balloon surface could carry drug particles to provide a desirable payload of the drug on the balloon surface. As already mentioned, an excipient can be dissolved in an aqueous media in which the drug particles are suspended. When the combined solution/suspension is dried the excipient forms a matrix in which the particles are held. The matrix allows for a relatively thicker loading of particles. At the time of delivery the matrix material readily dissolves leaving the particles at the tissue site.

Figure 3:
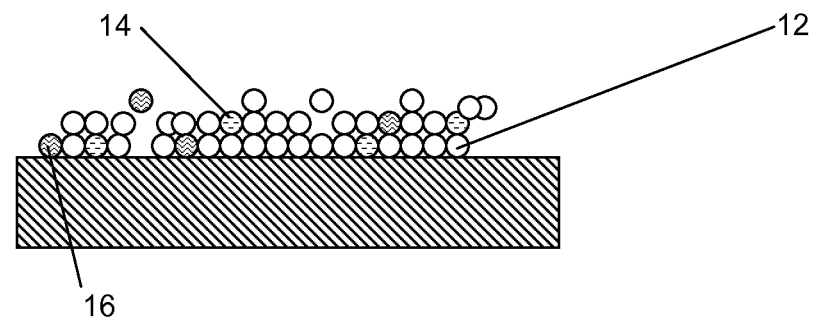
FIG. 3 Schematic depiction of a balloon surface coated with nanocrystalline drug particles and two types of tracer particles.
Figure 4:
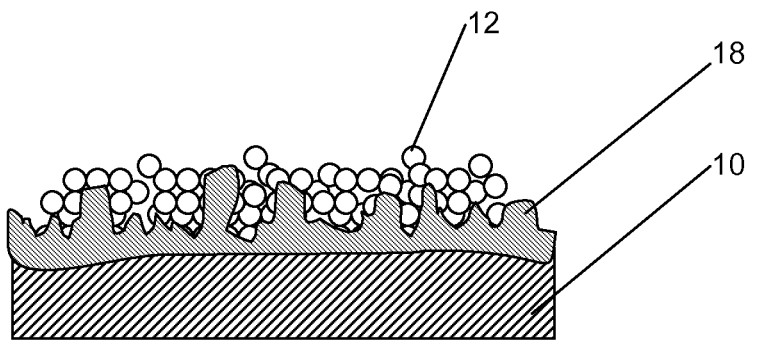
FIG. 4 Schematic depiction of a balloon surface coated with microfibrous rough surface and with nanocrystalline drug particles and tracer particles.

Another way to increase the drug particle loading involves texturizing the balloon surface. Instead of a smooth balloon surface, one can provide the balloon surface with a micro-rough (textured) surface, for example by spraying an initial polymer onto the balloon surface which leaves a rough permanent surface behind. This textured surface will remain permanent on the balloon surface. Illustrative are very soft urethane or silicon surfaces. FIG. 3 is illustrative. The balloon substrate material 10 is provided with a rough texture coating 18, the roughened texture providing crevices which allow retention of a relatively larger number of drug particles 12 on the surface. The surface particles, of course, may optionally include tracer particles not shown in this Figure.

A rough texture balloon surface can be created by using for example a inkjet printing system to provide the coating 18 at varied thickness. Another technique may be to dip-coat the balloon with a liquid composition after which the still-wet surface is blown dry by a strong air jet to provide a roughness produced by the turbulence of the air jet. Curable systems that are applied in a similar textured manner as liquids and then cured to permanently fix the texture are suited for providing such a textured coating 18, as are techniques involving use of polymer solutions in solvent that are set by evaporation.

In at least some embodiments the particles are applied subsequent to texturizing the device surface. However, in some circumstances, for instance if drug particles can be maintained in particulate suspension in a texture-forming composition, and also the cured or set texture matrix does not bond to the particles, a single application of a combination texture material and particle-containing composition may be practical for both texturizing the surface and loading that surface with the drug particles.

In yet another way to increase the drug particle loading, in between the spraying of the nano-particles on the balloon one can spray, alternatingly or simultaneously, secondary materials that act as a matrix material able to quickly dissolve in the body. The excipient materials discussed above are illustrative of such secondary materials. The solvent for this secondary material again should be one that does not dissolve the drug particles. The secondary excipient material so applied may penetrate between the particles or form a cap layer over the particles, depending on application technique, the concentration and viscosity of the applied composition, and the like.

Figure 5:
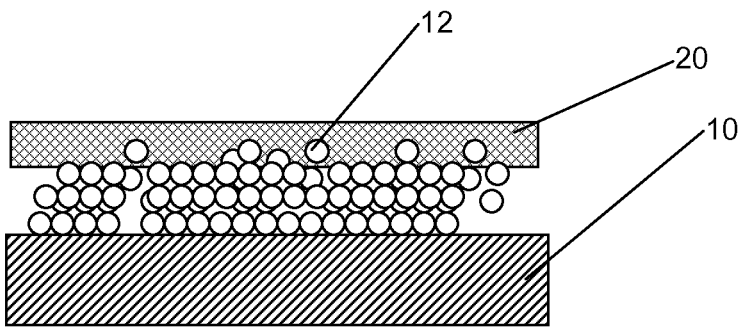
FIG. 5 Schematic depiction of a balloon surface coated with nanocrystalline drug particles and capped with brittle or soluble layer.

FIG. 5 illustrates a specific embodiment of the use of a secondary excipient material applied as top layer 20 on the layer of drug particles 12 to act a breakable lid. In some embodiments such a cap layer may have a thickness of 2 μm or less, for instance about 1 about 0.5 about 0.1 or about 0.01 Polymers or copolymers that have a good solubility in water and a molecular weight sufficient to slow dissolution of the coating enough to provide practical protection may be used. Other protective cap layers may be effective if they break up into fine particles upon balloon expansion. Protective cap layer thickness may be adjusted to give an acceptable dissolution and/or degradation profile.

In still another technique for increasing drug particle loading on a balloon surface, one can combine fibrinogen with the nanocrystals to provide an intertwined network of fibers and particles.

Another application technique is to spray a network of polymer fibers on the balloon surface by electrostatic spray methods producing a very open network. This fiber network can then be dipped in the suspension of the drug nanoparticles.

Although the invention has been described specifically as applied to balloon surfaces, it should be noted that the application techniques may be applied to produce drug particle coatings on other devices adapted for insertion into the body, for instance on permanent implants such as stents, grafts, neurocoils etc.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

What is claimed is:

1. A medical device, comprising:
a catheter shaft;
a balloon coupled to the catheter shaft, the balloon having an outer surface;
a drug disposed on the outer surface;
wherein the drug comprises crystalline drug particles mixed with a water-soluble excipient;
wherein the water-soluble excipient includes acetyl tributyl citrate; and
wherein the crystalline drug particles have a particle size in the range of from 0.01 μm to 2 μm.

2. The medical device of claim 1, wherein the crystalline drug particles comprise paclitaxel.

3. The medical device of claim 1, wherein the crystalline drug particles comprise everolimus.

4. The medical device of claim 1, wherein the water-soluble excipient comprises a water-soluble polymer.

5. The medical device of claim 1, wherein the balloon includes a textured surface.

6. The medical device of claim 1, further comprising marker particles admixed with the crystalline drug particles.

7. A drug delivery balloon catheter, comprising:
a catheter shaft;
a balloon coupled to the catheter shaft, the balloon having a balloon wall with an outer surface;
a drug coating disposed along the outer surface;
wherein the drug coating comprises crystalline particles and a water-soluble excipient material;
wherein the water-soluble excipient includes acetyl tributyl citrate; and
wherein the crystalline particles have a particle size in the range of from 0.01 μm to 2 μm.

8. The drug delivery balloon catheter of claim 7, wherein the crystalline particles comprise paclitaxel.

9. The drug delivery balloon catheter of claim 7, wherein the crystalline particles comprise everolimus.

10. The drug delivery balloon catheter of claim 7, wherein the outer surface is textured.

11. The drug delivery balloon catheter of claim 7, wherein the drug coating includes marker particles admixed with the crystalline particles.

12. A drug delivery balloon adapted for delivery of a drug to a site in a body passageway, the drug delivery balloon comprising:
a balloon wall with an outer surface;
a drug disposed on the outer surface;
wherein the drug is provided on the balloon as crystalline particles of the drug having a particle size in the range of from 0.01 μm to 2 μm; and
wherein the crystalline particles are present in mixture with acetyl tri-butyl citrate a citrate ester.

13. The drug delivery balloon of claim 12, wherein the crystalline particles comprise paclitaxel.

14. The drug delivery balloon of claim 12, wherein the crystalline particles comprise everolimus.

* * * * *